United States Patent [19]
Garman et al.

[11] Patent Number: 5,499,991
[45] Date of Patent: Mar. 19, 1996

[54] ENDOSCOPIC NEEDLE WITH SUTURE RETRIEVER

[75] Inventors: Gary Garman, La Verne, Calif.; James C. Y. Chow, Mount Vernon, Ill.

[73] Assignee: Linvatec Corporation, Largo, Fla.

[21] Appl. No.: 358,421

[22] Filed: Dec. 19, 1994

[51] Int. Cl.$^6$ .............................. A61B 17/04; A61B 17/28
[52] U.S. Cl. ............................................ 606/148; 606/207
[58] Field of Search ...................................... 606/138, 139, 606/148, 205, 206, 207, 222, 223

[56] References Cited

U.S. PATENT DOCUMENTS

| | | |
|---|---|---|
| 292,195 | 1/1884 | Austin . |
| 1,545,682 | 7/1925 | Nelson . |
| 1,583,271 | 5/1926 | Biro . |
| 2,738,790 | 3/1956 | Todt, Sr. et al. . |
| 2,959,172 | 11/1960 | Held . |
| 3,877,434 | 4/1975 | Ferguson et al. . |
| 4,372,302 | 2/1983 | Akerlund . |
| 4,641,652 | 2/1987 | Hutterer et al. . |
| 4,779,616 | 10/1988 | Johnson . |
| 4,781,190 | 11/1988 | Lee . |
| 5,015,250 | 5/1991 | Foster . |
| 5,149,329 | 9/1992 | Richardson . |
| 5,176,700 | 1/1993 | Brown et al. ............................ 606/207 |
| 5,181,919 | 1/1993 | Bergman et al. . |
| 5,201,741 | 4/1993 | Dulebohn . |
| 5,222,508 | 6/1993 | Contarini . |
| 5,222,977 | 6/1993 | Esser . |
| 5,250,054 | 10/1993 | Li . |
| 5,250,055 | 10/1993 | Moore et al. . |
| 5,312,422 | 5/1994 | Trott . |

FOREIGN PATENT DOCUMENTS

| | | |
|---|---|---|
| 2532242 | 2/1977 | Germany . |

OTHER PUBLICATIONS

Catalog, Needleless Arthroscopic Suturing, Ideal Suture Grasper, Innovasive Devices, Inc., 1994, 4 pgs.
Article Entitled "Selective Capsular Repair Using The Roc Anchor, Surgical Technique" Described by David W. Altchek, M.D., Innovasive Devices, Inc., 4 pgs.

*Primary Examiner*—Tamara L. Graysay
*Attorney, Agent, or Firm*—Gene Warzecha

[57] ABSTRACT

A suture retriever and method for manipulating suture during endoscopic surgical procedures. The suture retriever has an elongated housing provided with a needle tip and a lateral opening situated near the tip. A suture engaging hook is extendable through the lateral opening and away from the axis of the housing in order to snare a suture. The hook is situated at the distal end of an elongated flexible support which is pre-formed in order to enable the hook to be laterally displaced from the axis of the needle tip when the support is moved distally relative to the lateral opening. When a suture is engaged by the hook, the latter is retracted proximally in order to place and hold the suture adjacent the lateral opening.

9 Claims, 5 Drawing Sheets

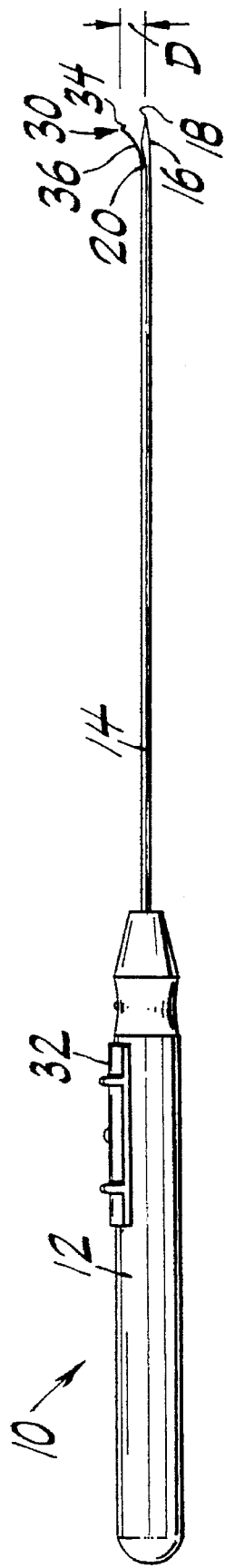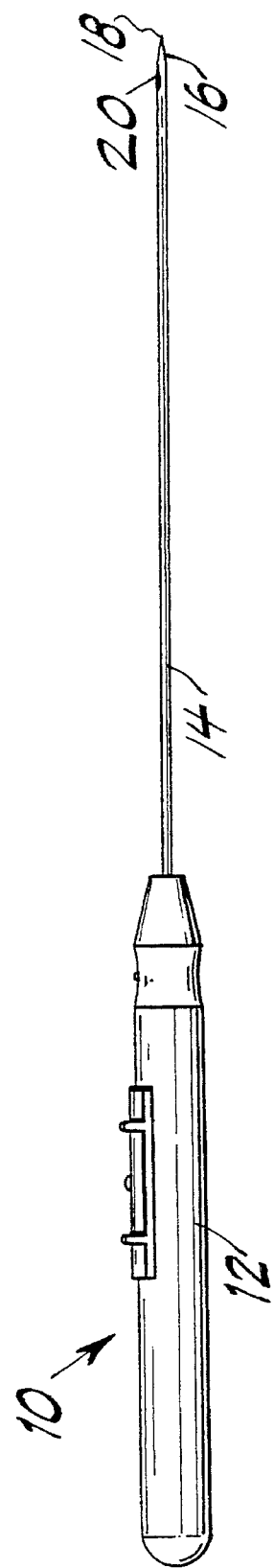

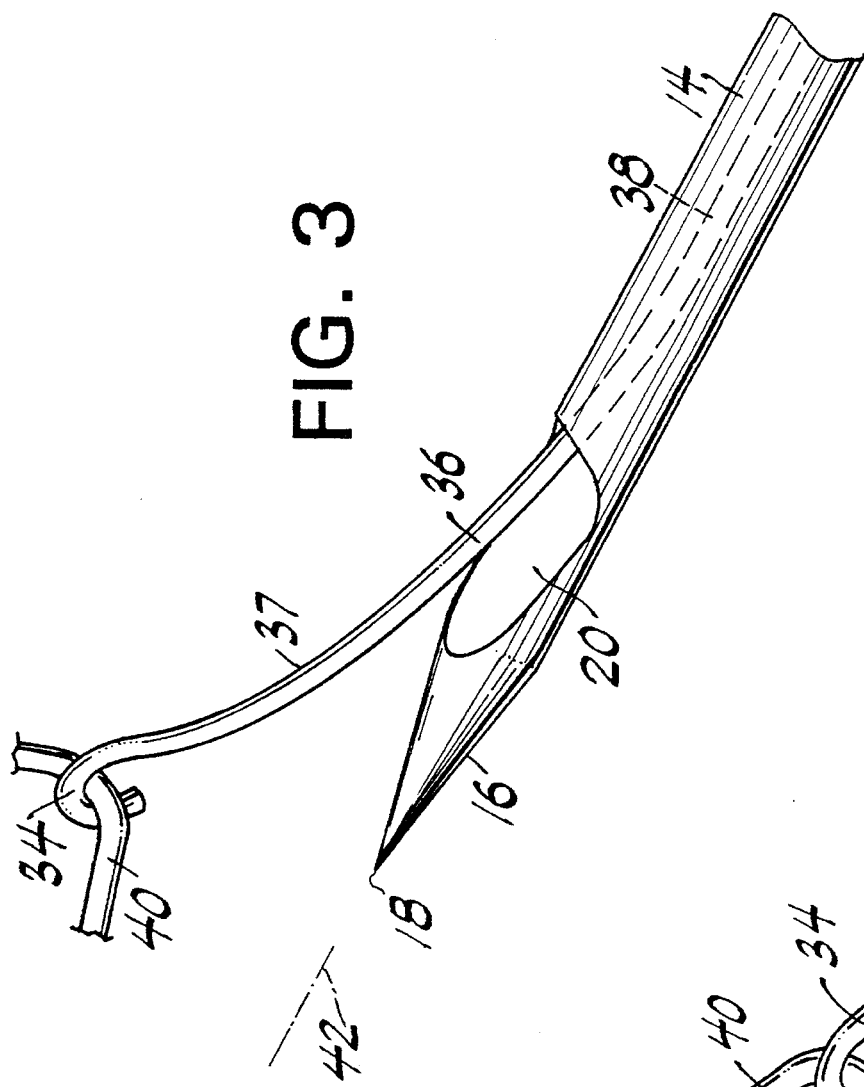

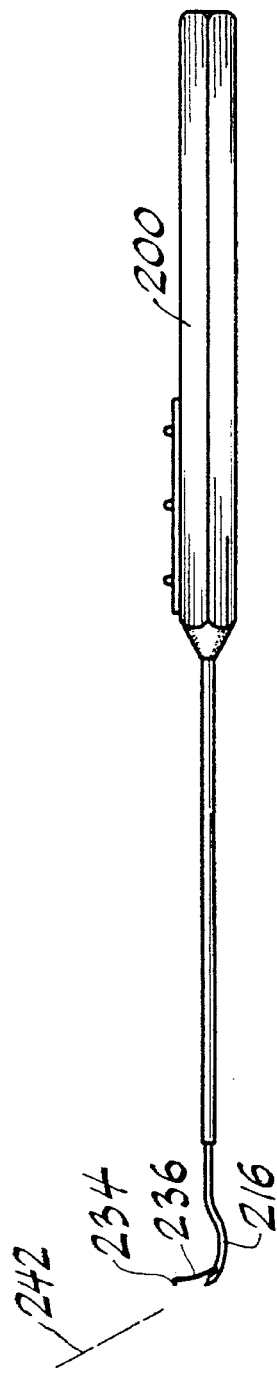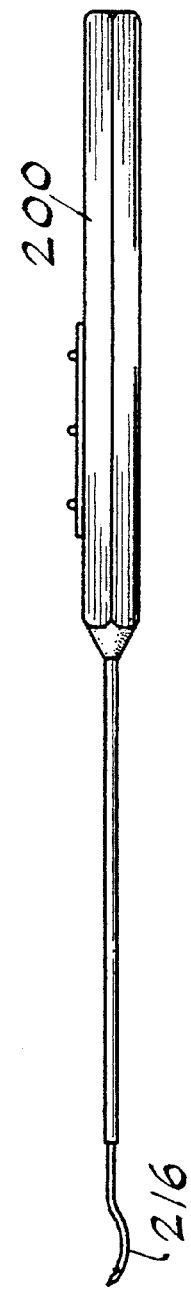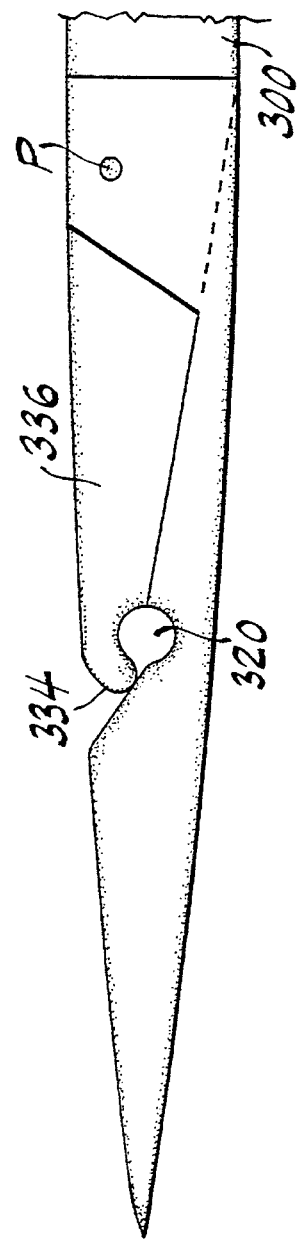

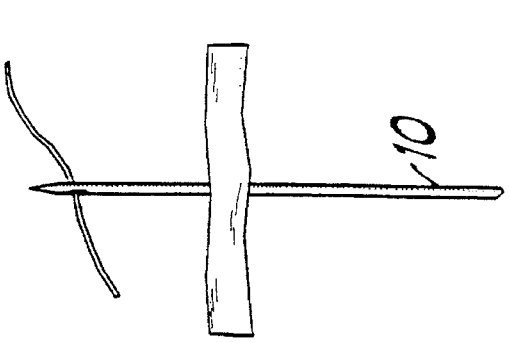
FIG. 10
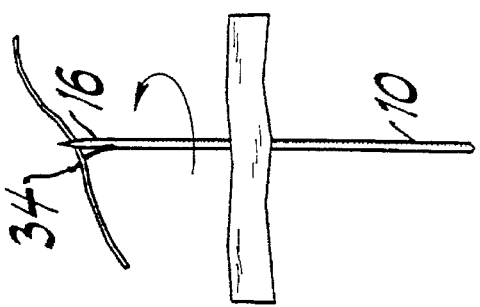
FIG. 11
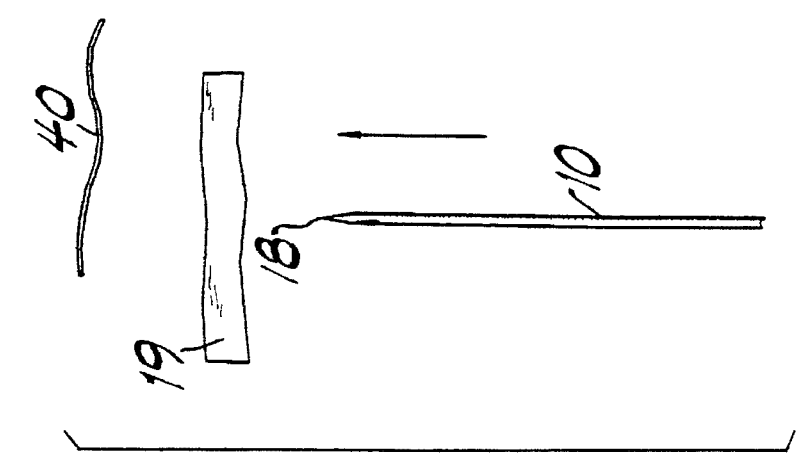
FIG. 12
FIG. 13

5,499,991

ENDOSCOPIC NEEDLE WITH SUTURE RETRIEVER

BACKGROUND OF THE INVENTION

1. Field of the Invention

This invention relates to devices and methods for endoscopically manipulating sutures during surgical procedures. More particularly, this invention relates to devices and methods for endoscopically suturing tissue.

2. Description of the Prior Art

Endoscopic suturing techniques and instruments have been developed in order to facilitate the suturing of tissue during endoscopic surgical procedures. The term "endoscopy" encompasses arthroscopy, laparoscopy, hysteroscopy, etc. and endoscopic surgery involves the performance of surgical procedures within a patient's body through small openings as opposed to conventional open surgery through large incisions. Access to a surgical work site within a patient's body is normally provided through one or more portals formed directly in the patient's body or through one or more cannulas inserted into the patient's body through small incisions. A chosen surgical procedure is carried out by a surgeon through the use of elongated instruments inserted through these cannulas and it often becomes necessary to suture selected tissue at the surgical work site.

Since the work site is only accessible through a small portal or cannula and since it is very difficult to tie sutures within the body, various devices and techniques have been developed to enable the surgeon to tie sutures endoscopically. For example, some procedures enable the surgeon to pass suture material through selected tissue, form a surgical knot extracorporeally and then move the knot with a knot pusher through the portal or cannula into position adjacent the desired tissue to be sutured. Some instruments used to pass the suture incorporate a hollow needle provided with some means to guide suture through the tissue pierced by the needle.

The procedure typically used to tie sutures endoscopically involves retrieving the end of the suture after it has been passed through the tissue site to be sutured. The retrieved suture end can then be manipulated with the other suture end to tie a knot. The retrieval of suture is sometimes accomplished by simply grasping it with regular forceps or other graspers or specific suture retrieval forceps having a suture capturing aperture formed at the distal tip when the forceps jaws are closed. Some suture retrievers are simply loops which extend from the tip of an elongated tube and which can be closed upon a suture passed through the loop. U.S. Pat. No. 5,250,054 (Li) discloses a suture retriever in the form of a knot tying device having an elongated inner rod slidably situated within an elongated outer sleeve. The distal end of the inner rod is provided with a pre-formed bend and the tip has a crochet-type hook to retrieve suture. These devices, however, require a separate needle to suture tissue. Therefore, to facilitate the process the needle and grasper are sometimes combined in one instrument. For example, a known prior art elongated needle/grasper which facilitates endoscopic suturing is described in U.S. Pat. No. 5,312,432 (Trott) entitled "Endoscopic Suturing Needle", assigned to the assignee hereof and incorporated herein by reference. This endoscopic suturing needle comprises an elongated tubular housing having a needle at the distal tip and a trigger mechanism to advance and retract the needle relative to the housing. The needle is pointed and flat and has a recess provided at a predetermined distance proximal to the needle tip. When the needle is fully retracted relative to the housing, the recess provides an opening to capture suture material therein. This allows the needle to either push or pull suture through selected tissue. Repeated manipulation of the suture can thus create the desired surgical stitch.

Another type of suturing needle is disclosed in U.S. Pat. No. 5,222,977 (Esser) in which the needle tip is stationary and a movable slide is provided to open and close a suture receiving recess spaced a predetermined distance from the needle tip. A similar mechanism is shown in German Patent No. 2532242 which discloses a cylindrical needle having a reciprocating internal slide member to open and close a recess spaced from the needle tip.

Another known suture retrieval instrument comprises a curved hollow tube having a distally extending suture snare. The device, known as the Ideal Suture Grasper marketed by Innovasive Devices, Inc., 100B South Street, Hopkinton, Mass. 01748, requires two components to capture suture and is only able to retrieve suture that is in line with the distal tip.

The means by which a strand of suture material can be grasped or retrieved with the prior art devices is limited because all of the known suture needle/retrieval devices have suture snaring means which are situated on or in line with the needle body. Consequently, the device must be manipulated close enough to the suture to guide the suture into a suture receiving recess so the recess can be closed to retain the suture to enable its manipulation. In an endoscopic procedure it is often difficult to manipulate the suturing needle close enough to the suture to accomplish this. Accordingly, it is an object of this invention to provide an endoscopic suturing needle which enables a surgeon to retrieve a suture spaced some distance laterally from the needle, without having to reposition the needle so as to place the suture in the recess or grasping structure.

It is also an object of this invention to produce an endoscopic suturing needle in which the suture snaring structure can be automatically deployed away from the axis of the needle tip in order to increase the volume of space within which the suture may be present and still be grasped.

It is also an object of this invention to provide a suture retriever for endoscopically retrieving suture material without the necessity of guiding the retriever as close to the suture as required by prior art devices.

It is another object of this invention to provide a suture retriever having an extended lateral reach in order to retrieve suture within a larger area than prior art devices.

It is still another object of this invention to provide a simplified endoscopic needle and suture retriever combination having an extended lateral reach in order to retrieve suture within a larger area than prior art devices.

SUMMARY OF THE INVENTION

These and other objects of the invention are achieved by the preferred embodiment disclosed herein which is a suture retriever comprising a handle having an elongated outer tube extending from the handle, the tube having an opening in its wall adjacent the distal end and facing in a direction perpendicular to said axis. An elongated rigid inner support member is slidably situated within the tube and is movable between a closed, retracted position, in which the member is at the proximal-most end of its range of motion, and an open, extended position in which the member is at the distal-most end of its range of motion. A pre-formed, elongated flexible support member is attached to the distal end of the elongated rigid inner support member. The flexible support member is constrained to conform to the shape of the elongated outer tube when the rigid support member is at its proximal-most position and is able to conform to its predetermined shape when the rigid support member is at its distal-most position. A single, suture-engaging distal tip in the form of a hook is attached to the flexible support member and is automatically positioned and laterally displaced from the opening in the tube at increasingly greater lateral distances from the axis as the inner support member is moved distally.

The invention is also embodied in the method of endoscopically retrieving suture comprising the various steps of using the aforementioned suture retriever. The steps comprise providing an elongated housing having a needle tip and a suture snare longitudinally and radially extendable from the housing when the suture snare is deployed. The steps further comprise piercing the tissue to be sutured with the needle tip in order to place it in proximity to a suture to be retrieved. The suture snare is then deployed from the housing and manipulated to engage a suture with a hook on the suture snare. The suture snare is then retracted towards the housing to trap the suture between the snare and the housing and the endoscopic needle is then removed from the tissue to pass the retrieved suture through the tissue. The method may additionally comprise the step of rotating the housing about its axis after the suture snare has been deployed in order to sweep the snare through a volume of space to thereby capture a suture extending through this volume.

BRIEF DESCRIPTION OF THE DRAWINGS

FIG. 1 is a side elevational view of an endoscopic suturing needle constructed in accordance with the principles of this invention showing the suture retriever in an open position.

FIG. 2 is a view of FIG. 1 showing the suture retriever in a closed position.

FIG. 3 is an exploded view of the distal tip of the endoscopic suturing needle of FIG. 1 in an open position showing a strand of suture adjacent the suture retriever.

FIG. 4 is an exploded view of the distal tip of the endoscopic suturing needle showing the suture retriever engaged with a strand of suture in the closed position.

FIGS. 7 and 8 are side elevation views of another alternate embodiment of the invention in open and closed positions, respectively.

FIG. 9 is a side elevation view of another alternate embodiment of the invention.

FIGS. 10, 11, 12 and 13 are diagrammatic drawings of one method of using the endoscopic suturing needle shown in FIG. 1.

DESCRIPTION OF THE PREFERRED EMBODIMENT

Figures 5, 6:
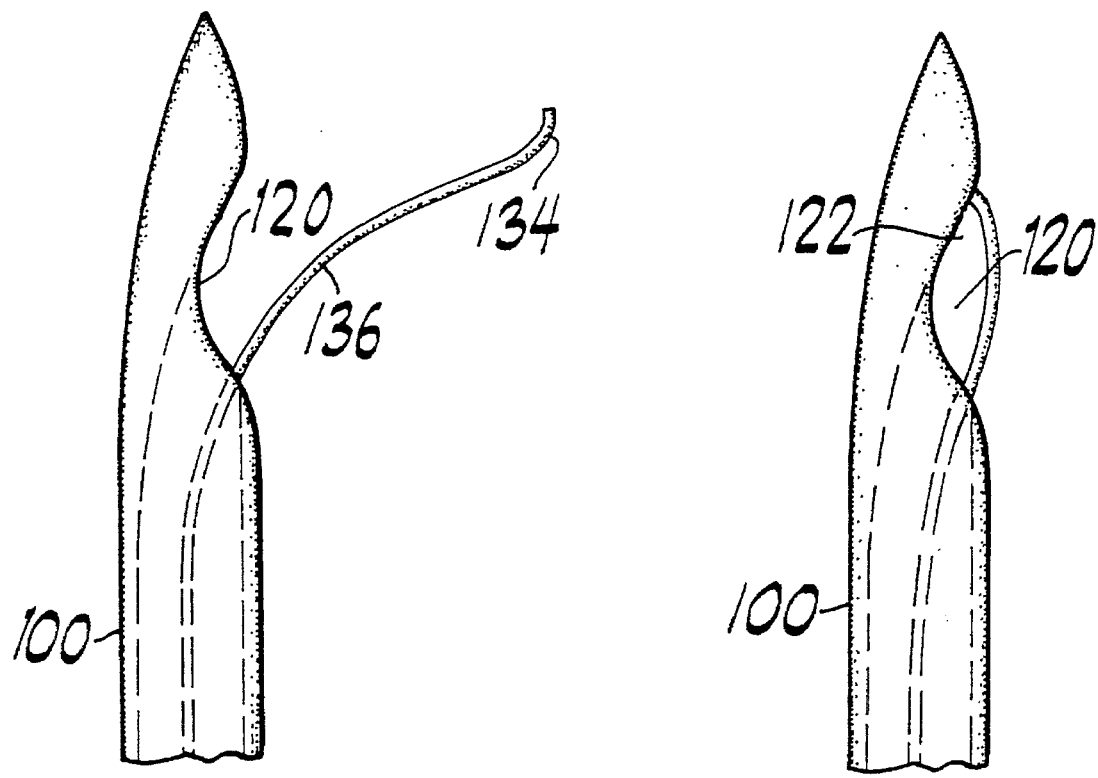
FIG. 5 is a view of the distal tip of an alternate embodiment of the endoscopic needle in the open position.
FIG. 6 is a view of FIG. 5 in the closed position.

Referring now to FIGS. 1 and 2, there is shown an endoscopic suturing needle 10 constructed in accordance with the principles of this invention. Needle 10 comprises a handle 12 having an elongated tubular housing 14 extending from one end thereof. Housing 14 terminates in a distal end 16 which, in the preferred embodiment, is provided with a needle tip 18. Housing 14 is also provided with a side-facing or lateral opening 20 adjacent distal end 16, proximal to needle tip 18. Opening 20 essentially serves as a suture receiving recess as well as an access aperture. Needle 10 also comprises a suture snaring assembly 30 comprising a thumb actuated trigger 32, a suture engaging distal tip or hook 34, a pre-formed hook support 36 and an elongated, rigid support member 38 (best seen in FIG. 3) extending between trigger 32 and pre-formed support 36.

As best seen in FIGS. 3 and 4, suture engaging hook 34 is, because of the particular shape of suture hook support 36, movable longitudinally and laterally relative to opening 20 in order to engage suture 40. Suture hook support 36 is flexible and pre-formed with a concave curved side 37 facing away from axis 42 in order to have a predetermined bend when it is deployed by being extended distally relative to opening 20 in order to present hook 34 at a predetermined lateral distance D away from the axis 42 of endoscopic suturing needle 10. The support 36 is flexible enough to be constrained to conform to the shape of housing 14 when it is retracted to nest hook 34 in or adjacent to opening 20. In the preferred embodiment, the pre-formed hook support 36 is attached to the distal end of a rigid elongated support shaft 38 joining it to trigger 32. Alternatively, hook support 36 may be an integral extension of support shaft 38 if suitable materials are utilized (for example, the entire length-of hook 36 and shaft 38 could be made of nitinol). Elongated support shaft 38 need only be sufficiently rigid to be able to move flexible support 36 longitudinally within a predetermined range sufficient to either retract it to the closed position shown in FIG. 4 or extend it to the open position shown in FIG. 3. The extent of the lateral displacement D of hook 34 relative to axis 42 is dependent upon the degree of the bend to which hook support 36 is pre-formed. The extent of the lateral displacement may range anywhere from an insignificant amount—in the event that hook support 36 is not pre-formed with any bend at all and is in effect a straight extension of a straight longitudinal support shaft (not shown)—to a greater than 90° bend in support 36 which would begin to face hook 34 away from axis 42 (not shown). In the preferred embodiment, the extent of preformation of hook support 36 is such that the bend of hook 34 faces axis 42 and is able to snare any suture within a target area T bounded by tip 16, hook support 36 and an imaginary line joining hook 34 to needle tip 18. It will be understood that, as needle 10 is rotated about axis 42, this target area sweeps through a 360° circle to create a significant, conical volume of space about the distal end of needle 10 within which suture 40 may be retrieved.

Referring now to FIGS. 5 and 6, an alternate embodiment 100 of the invention is shown in which the suture engaging distal tip attached to the end of pre-formed support 136 is shaped into a slightly curved end 134 rather than a distinct hook. In this embodiment, opening 120 is formed in a manner which is complementary to tip 134 in order to create a suture enclosing space 122 when support 136 is retracted.

As shown in FIGS. 7 and 8, an alternate embodiment of the invention is shown in the form of endoscopic suturing needle 200 having a curved distal end 216. The axis 242 of the tip of distal end 216 is aligned in a chosen direction at a predetermined angle relative to the axis of the handle. When a side-facing opening (similar to opening 20 of FIG. 1) is placed proximal to the tip of the curved distal end, the pre-formed hook 234 extends relative to the axis of the distal end and operates similarly to the straight embodiment of needle 10. As shown in FIGS. 7 and 8, endoscopic needle 200 is in all other respects similar to endoscopic needle 10 although the relative orientation of components at the distal end is different. It will be understood that the distal end of the needle may be formed in a variety of shapes (corkscrew, "U-turn", etc.).

As shown in FIG. 9, an alternate embodiment 300 of the invention may be made by replacing hook 34 and support 36 with a hinged support jaw 336. The distal end of jaw 336 is curved into a hook 334 which encloses a suture receiving recess 320 similar to opening 20 in function. It will be understood that jaw 336, hinged around pivot point P, is movable in a conventional manner from the handle of the instrument (not shown) and, when open, forms a target area between the distal tip of the open jaw and the body of the needle.

Referring to FIGS. 10 through 13, a method of using the endoscopic suturing needle of FIG. 1 is described. While the various steps of the method are not specifically shown as being endoscopic in the sense that neither a body cavity nor a cannula is shown, it will be understood that the steps it facilitate endoscopic suturing although the device and the method may be also used during open procedures. It will also be understood that the procedure is carried out under endoscopic visualization via a camera (not shown). As shown in FIG. 10, the tissue 19 to be sutured and through which suture is to be passed is pierced with needle 18 in order to place it in proximity to a portion 40 of suture on the side of the tissue where the suture is already situated. It will be understood by those skilled in the art that suture 40 may be situated in such a position for a variety of reasons: either the suture may have been passed through a cannula (not shown), it may have been previously placed partially as shown by a previous step of using needle 10 or a variety of other reasons. Once the needle is punctured through tissue 19 and in proximity to the suture as seen through an endoscopic camera, the needle may then be rotated about its axis as shown in FIG. 11 in order to enable suture 40 to be trapped in the target area between hook 34 and distal end 16. Once the suture is within the target area, the trigger 32 (FIG. 1) is proximally retracted in order to engage hook 34 on suture 40 and nest it (i.e. retain it either firmly or loosely) within opening 20 as shown in FIG. 12. Once the suture is so secured, needle 10 may be pulled proximally through the tissue as shown in FIG. 13. From this point, either end 40a or 40b of suture 40 may be pulled through the tissue to enable the ends to be tied together in a conventional manner or needle 10 may be passed through the tissue in a different location to create a mattress stitch (not shown).

While the preceding method has been described with the suture already in position on the other side of the tissue, it will be understood that the suture may be retained firmly or loosely within opening 20 prior to the needle being passed through the tissue (not shown). The suture may then be released and the needle may be withdrawn and repositioned through another portion of the tissue in order to retrieve the suture.

It will be understood that numerous other modifications and improvements may be made to the preferred embodiment of the invention disclosed herein without departing from the spirit and scope thereof.

What is claimed is:

1. A suture retriever comprising:

a handle;

an elongated outer tube attached to and extending from said handle, said tube having a distal end with an axis aligned in a predetermined direction relative to said handle and an opening in the wall of said tube adjacent said distal end and facing in a direction perpendicular to said axis;

an elongated rigid inner support member slidably situated within said outer tube;

means for moving said elongated inner support member between a closed, retracted position in which said elongated inner support member is at the proximal-most end of its range of motion, and an open, extended position in which said elongated inner support member is at the distal-most end of its range of motion; and a suture capturing member comprising:

a single, elongated flexible support member having a distal end and a proximal end, said flexible support member attached to the distal end of said elongated rigid inner support member and extendable through said opening, said flexible support member being preformed in a predetermined shape which enables it to be constrained to conform to the shape of said elongated outer tube when said rigid support member is at its proximal-most position and which enables it to conform to said predetermined shape when said rigid support member is at its distal-most position; and a curved suture-engaging distal tip attached to the distal end of said flexible support member, said suture-engaging distal tip curved towards said axis whereby said suture-engaging distal tip is automatically positioned and laterally spaced from said opening at increasingly greater lateral distances from said axis as said inner support member is moved distally.

2. A suture retriever according to claim 1 wherein said suture-engaging distal tip is formed into a hook.

3. A suture retriever according to claim 1 wherein said predetermined shape is such as to position said suture-engaging distal tip at a point distal to and laterally spaced from said opening when said rigid support member is at its distal-most position.

4. A suture retriever comprising:

a handle;

an elongated, hollow housing extending from said handle, said housing provided with a needle tip at its distal end, said housing having an axis and a suture receiving recess facing away from said axis and proximal to said distal end;

suture snare means movably mounted relative to and extendable away from said suture receiving recess for engaging suture for selectively retaining suture against said suture receiving recess when said suture snare means is moved toward said housing.

5. A suture retriever according to claim 4 wherein said suture snare means comprises a pivotably movable hook member.

6. The suture retriever of claim 4 wherein said suture snare means is longitudinally movable proximally and distally with respect to said housing and further comprises a distal hook.

7. The suture retriever of claim 6 wherein said suture snare means further comprises a flexible support having a distal hooked portion, whereupon when said suture snare means is moved proximally toward a retracted position, said suture receiving recess is adjacent said hooked portion for retention of a suture therebetween.

8. A method of endoscopically retrieving suture comprising the steps of:

providing an elongated housing having a needle tip and a suture snare longitudinally and radially extendable relative to said needle tip when deployed;

piercing tissue to be sutured with said needle tip to place it in proximity to a suture to be retrieved;

deploying said suture snare from a housing;

engaging a suture with a hook formed on said suture snare;

retracting said suture snare towards said housing;

trapping said suture between said suture snare and said housing; and removing said needle tip from said tissue to pass said retrieved suture through said tissue.

9. A method according to claim 8 further comprising the step of rotating said housing about its axis after said suture snare has been deployed in order to sweep said suture snare through a predetermined volume of ambient space surrounding said axis to thereby capture a suture extending through said volume.

* * * * *